(12) United States Patent
Lu et al.

(10) Patent No.: US 10,092,622 B2
(45) Date of Patent: Oct. 9, 2018

(54) **OCCIDIOFUNGIN, A UNIQUE ANTIFUNGAL GLYCOPEPTIDE PRODUCED BY A STRAIN OF *BURKHOLDERIA CONTAMINANS***

(71) Applicant: Mississippi State University Research and Technology Corporation, Mississippi State, MS (US)

(72) Inventors: Shien Lu, Starkville, MS (US); James L. Smith, College Station, TX (US); Frank Austin, Starkville, MS (US); Ganyu Gu, Melfa, VA (US)

(73) Assignee: MISSISSIPPI STATE UNIVERSITY, Starkville, MS (US)

( * ) Notice: Subject to any disclaimer, the term of this patent is extended or adjusted under 35 U.S.C. 154(b) by 0 days.

(21) Appl. No.: 14/806,121

(22) Filed: Jul. 22, 2015

(65) Prior Publication Data

US 2016/0008423 A1    Jan. 14, 2016

Related U.S. Application Data

(63) Continuation of application No. 12/800,922, filed on May 25, 2010, now abandoned.

(60) Provisional application No. 61/217,026, filed on May 26, 2009.

(51) Int. Cl.
*A61K 38/12* (2006.01)
*A61K 38/16* (2006.01)

(52) U.S. Cl.
CPC .............. *A61K 38/16* (2013.01); *A61K 38/12* (2013.01)

(58) Field of Classification Search
None
See application file for complete search history.

(56) References Cited

U.S. PATENT DOCUMENTS

2003/0130121 A1*  7/2003  Gerhardson ........... A01N 63/00
                                                          504/117

OTHER PUBLICATIONS

Lu et al. ('Isolation and identification of Rhizobacteria antagonistic to plant fungal pathogens' Phytopathology v95(6) 2005 pp. s62-s63).*
Gu et al. ('Biosynthesis of an antifungal oligopeptide in Burkholderia contaminans strain MS14' Biochemical and Biophysical Research Communications 380 (2009) pp. 328-332).*
Roemer et al. ('Antifungal drug development: challenges, unmet clinical needs, and new approaches' Cold Springs Harbor Perspectives in Medicine v4 a019703 2014 pp. 1-14).*
Alberts et al. (Molecular Biology of the Cell. 4th edition, New York: Garland Science; 2002; retrieved from http://www.ncbi.nlm.nih.gov/books/NBK26917/ on Mar. 2, 2015, 10 pages).*
Biology tutor (retrieved from http://biology.tutorvista.com/animal-and-plant-cells/cell-wall.html on Jun. 8, 2016, 5 pages).*
Online textbook of bacteriology (retrieved from http://textbookofbacteriology.net/medical.html on Jun. 8, 2016, 3 pages).*
UCIPM (retrieved from http://www.ipm.ucdavis.edu/PCA/pcapath.html on Jun. 8, 2016, 6 pages).*

* cited by examiner

*Primary Examiner* — Karlheinz R Skowronek
*Assistant Examiner* — Ronald T Niebauer

(57) ABSTRACT

The present invention is directed to novel antifungal glycopeptide compounds and salts thereof produced by a strain of *Burkholderia contaminans* useful for preventing or treating fungal infection or disease in animals and plants and the bacterial strain that produces the compounds.

15 Claims, 14 Drawing Sheets

| Organism | MIC (µg/mL) | MIC₅₀ (µg/mL) | Pathogen |
|---|---|---|---|
| Alternaria alternata | 8 | 1 | Plant and Animal |
| Aspergillus fumigatus | 8 | 1 | Animal |
| Aspergillus niger | 4 | 0.25 | Plant and Animal |
| Fusarium oxysporum | >32 | 16 | Plant |
| Geotrichum candidum | 8 | 4 | Plant and Animal |
| Macrophomina phaseolina | 2 | 0.25 | Plant |
| Microsporum gypseum | 4 | 1 | Animal |
| Penicillium sp. | 32 | 16 | Plant and Animal |
| Pythium spinosum | 1 | 0.5 | Plant |
| Pythium ultimum | 2 | 1 | Plant |
| Rhizoctonia solani | 2 | 0.5 | Plant |
| Trichophyton mentagrophytes | 4 | 2 | Plant and Animal |

FIG. 5A

OCCIDIOFUNGIN, A UNIQUE ANTIFUNGAL GLYCOPEPTIDE PRODUCED BY A STRAIN OF *BURKHOLDERIA CONTAMINANS*

CROSS-REFERENCES TO RELATED APPLICATIONS

This application is a continuation of co-pending U.S. patent application Ser. No. 12/800,922, filed May 25, 2010, which claims priority from U.S. Provisional Patent Application Ser. No. 61/217,026 filed May 26, 2009. The entirety of both applications is incorporated herein by reference.

STATEMENT OF GOVERNMENT SUPPORT

This invention was made with government support under 0204332 awarded by the Cooperative State Research, Education, and Extension Service, USDA. The government may have certain rights in the invention.

FIELD OF THE INVENTION

This invention relates to the field of antifungal compounds and their therapeutic use in the prevention or treatment of fungal infections and diseases. The invention relates to the use of the novel antifungal compounds as pharmaceutical and agricultural fungicides for animals and plants. The invention further relates to the bacterial strain that produces the new antifungal compounds.

BACKGROUND OF THE INVENTION

The present invention provides novel antifungal glycopeptides compounds for preventing or treating fungal infection and at least one novel amino acid residue related thereto. The present invention in a preferred embodiment also provides a pharmaceutical and agricultural composition that comprises the novel compounds and salts thereof for treating or preventing fungal infection. The invention in a further embodiment provides for the new bacterial strain that produces the new antifungal compounds.

There is a growing demand for new antifungals, given the increasing prevalence of pathogens resistant to current antifungal agents. Four major therapeutic groups of antifungal agents currently exist: polyene antifungals, azole antifungals, allylamine antifungals, and the cchinocandins. The first three groups primarily target ergosterol production or bind to ergosterol. disrupting the fungal membrane. Ergosterol, much like cholesterol found in mammalian cells, is important for maintaining proper cell permeability and fluidity. The echinocandins, the fourth group, are synthetically-modified lipopeptides that originate from the natural compound echinocandin B produced by *Aspergillus nidulans*. In fungi, two covalently cross-linked polysaccharides, (1,3)-β-glucan and chitin, form the primary scaffold that is responsible for the structural integrity and shape of the cell wall. The cchinocandin class of antifungal agents inhibit (1,3)-β-glucan synthase, an enzyme complex that polymerizes uridine diphosphate glucose into (1,3)-β-glucan polymers.

A striking feature of some strains of *Burkholderia* is production of various antifungal compounds, which make the organism potentially useful for management of fungal diseases. However, isolation of *Burkholderia* spp. from cystic fibrosis patients reclassified them as opportunistic pathogens, consequently preventing the direct use of the bacteria for fungal disease management. Isolation and identification of antifungals responsible for the observed plant-disease suppression activities of the *Burkholderia* strains will provide important avenues for the development of biological-based fungicides, while eliminating potential health risks from using the bacteria directly. Novel antifungals are needed because of the importance of fungal infections in immunocompromised patients, and the limitations of currently-available antifungal agents regarding their spectra of activity and toxicities. In addition, new antifungals arc crucial for food preservation and production of a sufficient and affordable food supply. In this disclosure, we characterize the structure and activity of a new antifungal compound named occidiofungin, meaning fungal killer. The complete covalent structure of the anti fungal has been elucidated by TOCSY, NOESY, ROESY, and HSQC 2D NMR spectroscopy experiments. Occidiofungin's antifungal activity against a variety of animal and fungal pathogens has been tested and proven. Additionally, aberrant membrane morphology, similar to what has been reported for the cchinocandins class of antifungals, was observed following exposure to sub-lethal concentrations of occidiofungin, suggesting that occidiofungin also targets the cell envelope. This work provides a substantial base for future experiments aimed at understanding the compound's mode of action, as well as investigating occidiofungin's pharmaceutical and agricultural potential.

As a result, a need exists in the field of fungicides for new antifungal compounds effective against animal and plant pathogens that are resistant to typical fungicidal agents. The present invention provides such a compound and composition.

SUMMARY OF THE INVENTION

The present invention provides for novel antifungal cyclic glycopeptide compounds with the name occidiofungin, a novel amino acid attached thereto, and a composition comprising such compounds. The present invention is effective against a broad range of fungal pathogens affecting humans, animals, and plants. Moreover, the present invention disrupts normal fungal membrane morphology. The present invention also provides for a novel bacterial strain that produces the new anti fungal compounds.

The present invention was purified from bacterial strain *Burkholderia contaminans* and includes eight (8) amino acid residues. Attached to one amino acid is an acyl group and a xylose sugar. An antifungal composition comprises the novel compound(s) and salts thereof and at least one acceptable carrier or diluent for subject administration. A method of treating fungal infection or disease comprises administration of the compound and composition to a subject for a time and under conditions effective for eliminating or ameliorating the infection.

With the foregoing and other objects, features, and advantages of the present invention that will become apparent hereinafter, the nature of the invention may be more clearly understood by reference to the following detailed description of the preferred embodiments of the invention and to the appended claims.

BRIEF DESCRIPTION OF THE DRAWINGS

These drawings accompany the detailed description of the invention and are intended to illustrate further the invention and its advantages. The drawings, which are incorporated in and form a portion of the specification, illustrate certain preferred embodiments of the invention and, together with the entire specification, are meant to explain preferred embodiments of the present invention to those skilled in the art:

FIG. 5A is a tabular illustration of spectrum of activity for occidiofungin. MIC values are presented for several plant and animal pathogens. MIC and MIC50 represent 100% growth inhibition and >50% growth inhibition, respectively.

DETAILED DESCRIPTION OF THE INVENTION

Figure 1A:
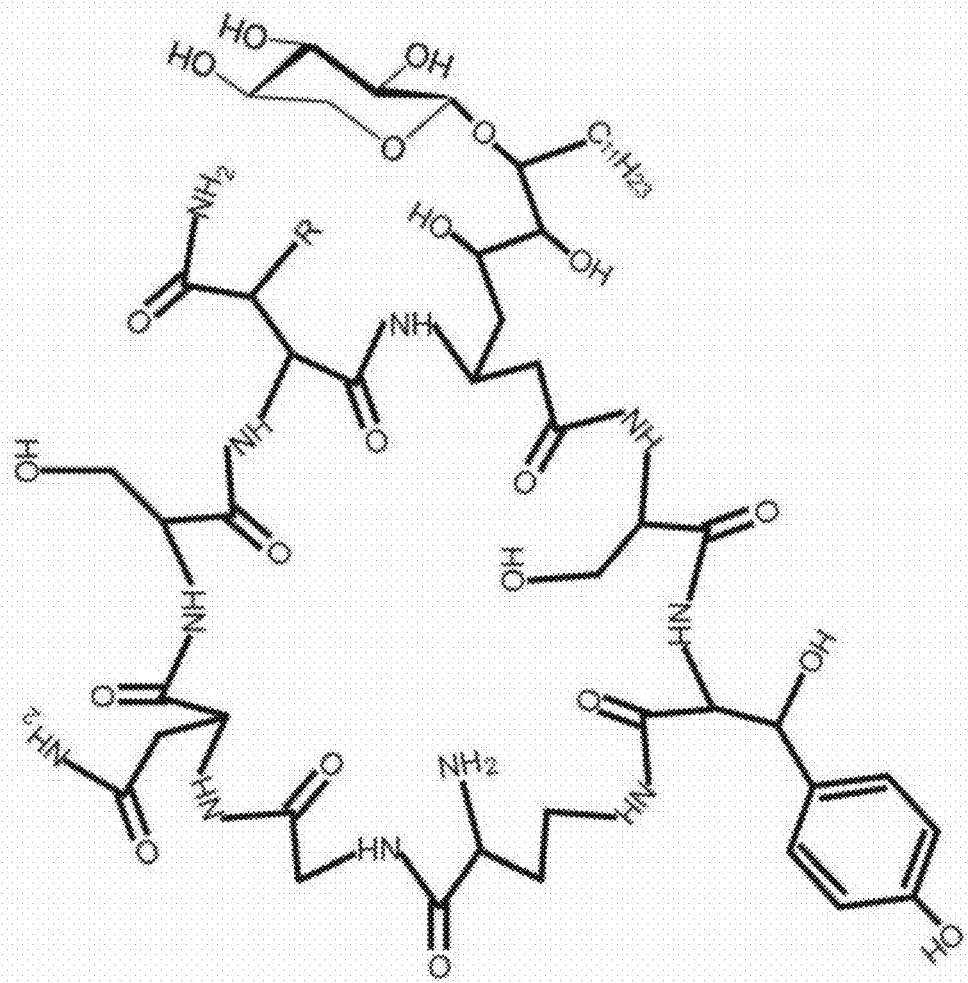
FIG. 1A is an illustration of the covalent structure of occidiofungin. Representative structures of occidiofungin A and occidiofungin B are shown.

The novel antifungal cyclic glycopeptide compounds of the present invention are effective against a broad range of fungal infections. The compound structures are disclosed herein, as well as the structure of at least one novel amino acid attached thereto.

In another embodiment of the present invention, an antifungal composition comprises the novel compound(s) and salts thereof and at least one pharmaceutically or agriculturally acceptable carrier or diluent for administration to human, animal, and/or plant subjects in need of fungicidal therapy and treatment.

In yet another embodiment, the present invention provides for a new isolated bacterial strain that produces anti fungal compounds including the new anti fungal compounds described herein.

For the purposes of this disclosure, abbreviations arc as follows: NMR, nuclear magnetic resonance; NOE, nuclear Overhauser effect; NOESY, nuclear Overhauser enhancement spectroscopy; TOCSY, total correlation spectroscopy; COSY, correlation spectroscopy; ROESY, rotational frame nuclear Overhauser effect spectroscopy; HSQC, heteronuclear single quantum coherence; ESI-MS, electrospray ionization mass spectrometry; MS/MS, tandem mass spectrometry; GC, gas chromatography-mass spectrometry; NRPS, nonribosomal peptide synthetases; NAA, novel amino acid; and MIC, minimum inhibitory concentration.

Molecular terms have their common meaning unless specified otherwise. The term "acyl" is defined as a carbonyl radical attached to an alkyl, alkenyl, alkynyl, cycloalkyl, heterocycyl, aryl, or heleroaryl group, examples including but not limited to radicals such as acetyl and benzoyl. The phrase "therapeutically effective amount" is defined as a dosage sufficient to induce a fungicidal effect upon fungi contacted by the compounds or composition. The amount of the pharmaceutical or agricultural composition that is therapeutically effective depends on the ingredients and components comprising the composition and the treatment philosophy.

For the present invention, bacterial strain *Burkholderia contaminans* MS14 was isolated from soil that suppressed brown patch disease of lawn grass. A novel antifungal compound was purified from the liquid culture of this bacterium. Complete covalent structures of two purified closely-related antifungal compounds were determined by the experiments of TOCSY, NOESY, ROESY, 13C HSQC 2D NMR, and ESI-MS and GC. The analysis of monoisotopic masses of the purified preparation indicated presence of two related compounds with masses determined to be 1199.543 Da and 1215.518 Da; the difference corresponds to the mass of an oxygen atom. GC analysis identified a xylose sugar attached to the antifungal compound. NMR experiments revealed that the compound is cyclic and composed of eight amino acids, two of which are β-hydroxy derivatives of Tyr and Asn, and one being a novel amino acid. The novel amino acid serves as the scaffold for the attachment of the xylose sugar and a short acyl chain. The spectrum and concentration of antifungal activity was determined using a microliter plate assay. The antifungal compound demonstrated potent antifungal activities against a broad panel of fungal plant and animal pathogens, as well as two *Pythium* spp. Microscopic observations showed that the antifungal compound disrupts normal membrane morphology. The fungal cells fill with large inclusion bodies and the membrane becomes irregularly shaped and swollen following the exposure to sub-inhibitory concentrations of the antifungal compound. Our data support the identification of the novel fungicide and the compound has been named occidiofungin, meaning fungal killer.

*Burkholderia contaminans* strain MS14 was previously isolated from disease-suppressive soil, a soil in which the soil-borne pathogen causes little or no damage to the host plant. Initial characterization of this strain showed that it inhibited the growth of a broad range of fungal pathogens. Subsequently, transposon mutagenesis identified the genomic region responsible for the antifungal activity, and a 56-kb genetic DNA fragment was sequenced and partially deposited into GenBank with the accession number: EU938698. This genomic region contains several open reading frames, some of which encode regulatory proteins, a cyclic peptide transporter, a glycosyltransferase, a transaminase, and nonribosomal peptide synthetase (NRPS) catalytic modules. The antifungal compound was then isolated and amino acid analysis confirmed that the backbone of the antifungal compound is an oligopeptide that is synthesized via a NRPS mechanism.

Experimental Procedures

All chemicals were purchased from Sigma (St. Louis, Mo.) and were the highest grade, unless otherwise stated. Occidiofungin was produced and purified as previously described.

Mass Spectrometry. The antifungal compounds in the active fractions were analyzed by electrospray mass spectrometry (ESI-MS) using a Micromass Q-TOF II mass spectrometer. The compounds were dissolved in 50/50 acetonitrile/water (v/v) with 0.1% formic acid and injected into a 1 µL/min flow of the same solvent using a Harvard syringe pump. The flow was sprayed using the nano-LC interface. Tandem MS (MS/MS) was performed with singly-charged ions using standard collision energy (34 V) and higher collision energy (50 V).

Monosaccharide compositional analysis. The monosaccharide in the purified occidiofungin was determined as trifluoroacetate of methylglycoside by gas-liquid chromatography. The analyses were performed with a gas chromatograph (Model 5890. Hewlett-Packard, Sacramento, Calif.) equipped with a 25-m fused silica (0.22-mm inner diameter) OV-1701 WCOT column (Chrompack, Bridgewater, N.J.) and electron capture detector. Sugar standards (pentoses, hexoses, N-acetylaminohexoses) were processed at the same time as the test compounds and the sugar in occidiofungin was determined based on comparison of its chromatographic profile with those of the standards. Sorbitol was used as internal standard.

NMR spectroscopy. Occidiofungin is not soluble in aqueous solutions at concentrations required for NMR. Therefore, 5 mM samples of occidiofungin were prepared in 50% acetonitrile-d3 (Cambridge Isotopes) and 50% water in a total volume of 700 µL. The NMR data were collected on Varian NMR System with Cold Probe™ spectrometer, operating at a proton frequency of 800 MHz. The resonances were assigned according to standard methods using COSY, TOCSY and NOESY experiments. ROESY and $^{13}$C-HSQC experiments were used to clarify some areas of ambiguity in the TOCSY and NOESY spectra. TOCSY, NOESY and $^{13}$C HSQC NMR experiments were collected at 25° C. and the ROESY experiment was collected at 4° C. The carrier frequency was centered on the water resonance, which was suppressed using the very efficient double-pulsed field gradient selective echo technique. A 1.5 s relaxation delay was used between scans. The TOCSY experiment was acquired with a 60 ms mixing time using the DIPSI-2 sequence. The NOESY and ROESY experiments were acquired with 400 ms and 100 ms mixing times, respectively. The parameters for collecting the HSQC spectrum were optimized to observe aliphatic CH groups (transfer delay time adjusted for a 140 Hz coupling constant and $^{13}$C offset set to 35 ppm). The spectral sweep width for the TOCSY, NOESY, and ROESY was 9000 Hz (11.25 ppm) in both dimensions. The spectral sweep widths for HSQC were 9000.0 Hz (11.25 ppm) in the proton dimensions and 21,200.0 Hz (105.5 ppm) for the carbon dimension. All 2D data were collected with 8192 complex points in the acquisition dimension and between 320 and 512 complex points for the indirect dimensions, except for the HSQC which was collected with 1024 and 192 complex points in the direct and indirect dimension, respectively. Phase sensitive indirect detection for NOESY, ROESY and TOCSY experiments was achieved using the method of States-TPPI. A gradient-selected sensitivity-enhanced pulse sequence was used for collecting the HSQC spectrum. $^1$H chemical shifts were referenced to acetonitrile (1.93 ppm). Data were processed with nmrPipe by first removing the residual water signal by deconvolution, multiplying the data in both dimensions by a squared cosine function or a squared cosine function with a 608 shift (for the $^1$H dimension of HSQC), zerofilling once, Fourier transformation, and baseline correction. Data were analyzed with the interactive computer program NMRView. The NOE cross-peak intensities were measured in NMRView. Distances were calibrated using the relationship $r_{ab}^6 = r_{cal}^6 (V_{cal}/V_{ab})$, where $r_{ab}$ is the distance between atoms a and b, $V_{ab}$ is the NOESY a to b cross-peak volume, $r_{cal}$ is a known distance, and $V_{cal}$ is the corresponding volume of the NOESY calibration cross-peak. The distance used for calibrations was the β-hydroxy Tyr4 $H^δ$ and $H^ε$ aromatic protons (2.46 Å).

Microbial organisms. Fungal strains were obtained from collections at Mississippi State University's Veterinary Medical Research and Diagnostic Laboratory System and Entomology and Plant Pathology Department or were purchased from the American Type Culture Collection (Manassas, Va.). Fungal isolates used in this study were *Alternaria alternata, Aspergillus fumigatus, Aspergillus niger; Fusarium oxysporum* f. sp. lycopersici ATCC9848, *Geotrichum candidum* F-260, *Macrophomina phaseolina* 61, *Microsporum gypseum, Penicillium* sp., *Rhizoctonia solani* MSCOT-I, and *Trichophyton mentagrophytes*. In addition, two *Pythium* species were tested: *Pythium spinosum* 472-04 and *Pythium ultimum* 671-04.

Antifungal susceptibility testing. Minimum inhibitory concentrations were determined by agar micro-dilution testing. Occidiofungin was serially two-fold diluted (32 μg/mL to 62.5 ng/mL) with sterile water and was added to flat bottomed 12 well plates. One (1) mL of Sabouraud dextrose agar Difco™ (BD Diagnostics, Franklin Lakes, N.J.) was added to each well. Once the agar solidified, the plates were stored inverted at 4° C. until used. Fungal cultures were grown on 100×15 mm Sabouraud dextrose agar plates (Thermo Fisher Scientific Remel Products, Lenexa, Kans.) at 22° C. for 7 days. A circular punch, containing a 1 cm in diameter plug of the fungi from the agar plate, was made from an area of the plate having a confluent growth of the fungi. The plug was place in 3 mL of PBS and ground with approximately 30 strokes of a Ten-brock homogenizer. Five (5) μL of the supernatant was placed in the center of each well and allowed to dry before incubating the microtiter plates at 22° C. Minimum inhibitory concentrations were measured at 48 hours for each species, except for *Trichophyton mentagrophytes*, which was measured at 72 hours. MICS were determined as the lowest concentration that inhibited visible fungal growth. $MIC_{50}$ values were determined as a concentration that visibly reduced colony growth by more than 50% (in diameter) as compared to the control.

Microscopy. The fungi growing in flat bottomed 12 well plates described above were used for examination of the effects of occidiofungin on the fungal hyphae and arthrospores. For each of the fungi, the hyphae or arthrospores with an observed $MIC_{50}$ at 48 hours growing next to the MIC well were used for preparation of light microscopy and transmission electron microscopy (TEM) slides. For light microscopy, lactophenol cotton blue solution (Sigma) was used as a positive stain and mounting medium for the slide. For TEM, the *G. candidum* samples were fixed at 4° C. with 2.5% glutaraldehyde in 0.1 M phosphate buffer (pH 7.2). After being rinsed with the buffer, specimens were post-fixed with 2% osmium tetroxide in the phosphate buffer. The specimens washed with the phosphate butler were dehydrated in graded ethanol serials (50-100%), and then embedded in Spurr's resin. Thin sections generated with a Reichert-Jung Ultracut E Ultramicrotome (60-90 nm) were double stained with uranyl acetate and lead citrate as described previously. The grids were observed under a transmission electron microscope Jeol JEM-100CX11 (Joel Ltd., Tokyo, Japan). Images were taken at magnifications between 5,000 and 8,000.

Results

Occidiofungin is a cyclic glycopeptide. High-resolution mass spectrometry data revealed the existence of two structural variants of the antifungal peptide; one having a monoisotopic mass of 1,199.543 Da and the other having a monoisotopic mass of 1,215.518 Da which corresponds to the addition of oxygen to the first compound. These masses are in accordance with the elucidated structure (calculated monoisotopic masses of 1,199.5584 and 1,215.5533) shown in FIGS. 1A and 1B. Given the presence of two structural variants, the variants of the antifungal compound are referred to as occidiofungin A (1,199.5584 Da) and occidiofungin B (1,215.5533 Da). ESI-TOF MS/MS analysis of the antifungal compound was inconclusive, as the standard collision energy resulted only in the loss of glycan and the high collision energy that was required to fragment the antifungal compound produced a complex series of daughter ions. However, the fact that high energy of dissociation was required for fragmentation to occur suggests that the compound is a cyclic peptide. A standard dissociation method resulted only in a loss of 149 Da from the parental ion, indicating the presence of a pentose sugar. GC analysis revealed that the sugar attached to the oligopeptide is a xylose (FIGS. 2A and 2B). As previously reported, amino acid analysis revealed the presence of a lysine. However, we subsequently revealed that this residue is a 2,4-diaminobutyric acid (DABA). An attempt to digest the peptide with trypsin was unsuccessful, which supports our reassignment of the residue (data not shown). Failure to linearize the antifungal peptide prevented subsequent ESI-MS analysis.

Figure 3A:
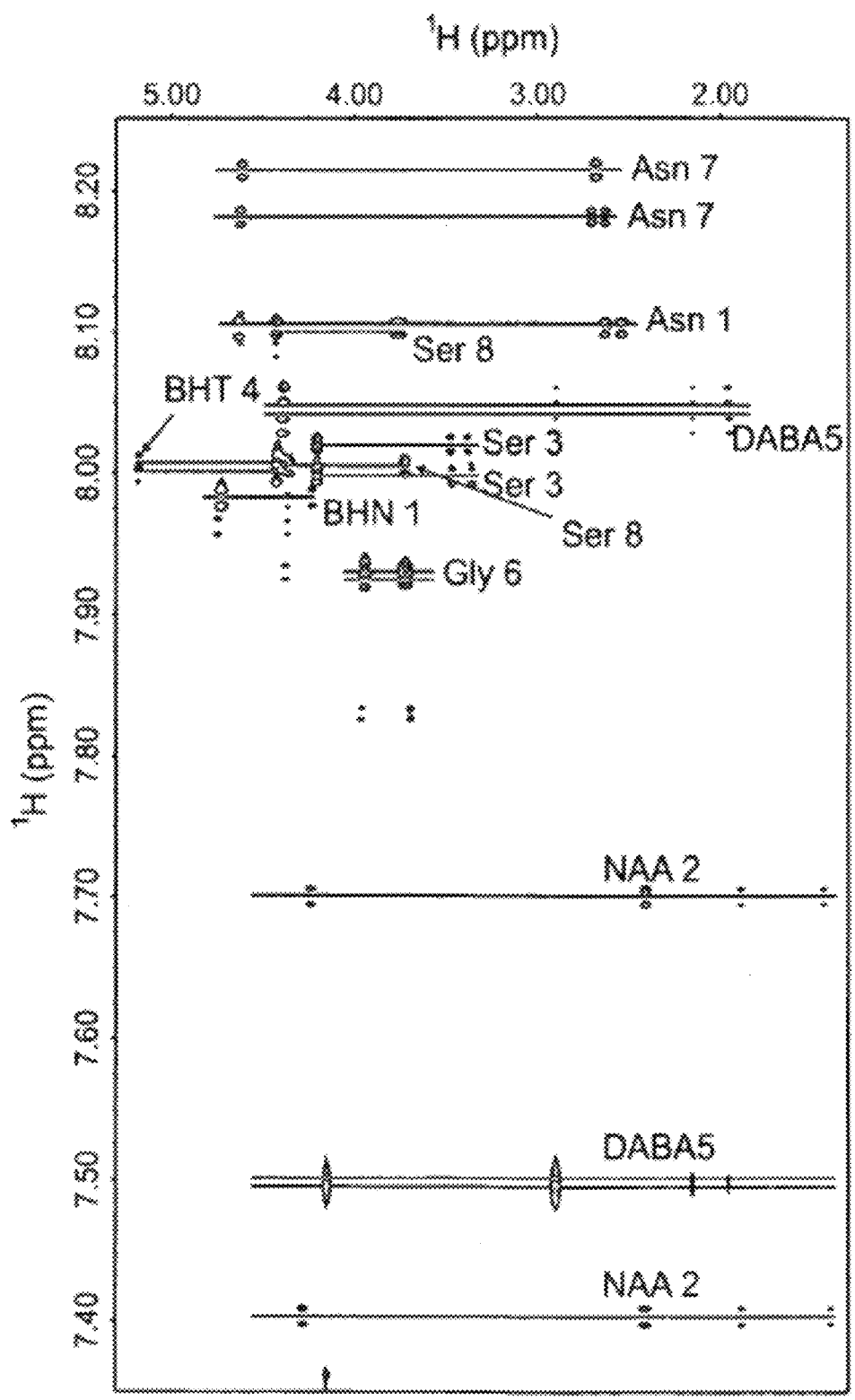
FIG. 3A is a graphical illustration of the TOCSY NMR spectra of occidiofungin. Expansion of the TOCSY 2D NMR spectra shows the amide to alpha, and amide to side chain spin systems for each assigned residue in occidiofungin A (black) and occidiofungin B (grey).

NMR proved to be the definitive method for determining the structure of the antifungal oligopeptide. To determine the complete covalent structure of the antifungal peptide, we collected TOCSY, NOESY, ROESY, and HSQC data. The TOCSY and NOESY datasets provided unambiguous sequential assignments and the ROESY and HSQC dataset was used as supporting evidence to the proton-based assignments. TOCSY/NOESY datasets revealed the presence of 13 distinct spin systems in the amide proton frequency of the spectrum. This number of spin systems is more than expected for an oligopeptide with a mass of 1199 and 1215 Da. Further analysis of the data set revealed that the oxidized variant, occidiofungin B, has several distinct spin systems in the amide frequency of the TOCSY spectrum (FIG. 3A).

Figure 1B:
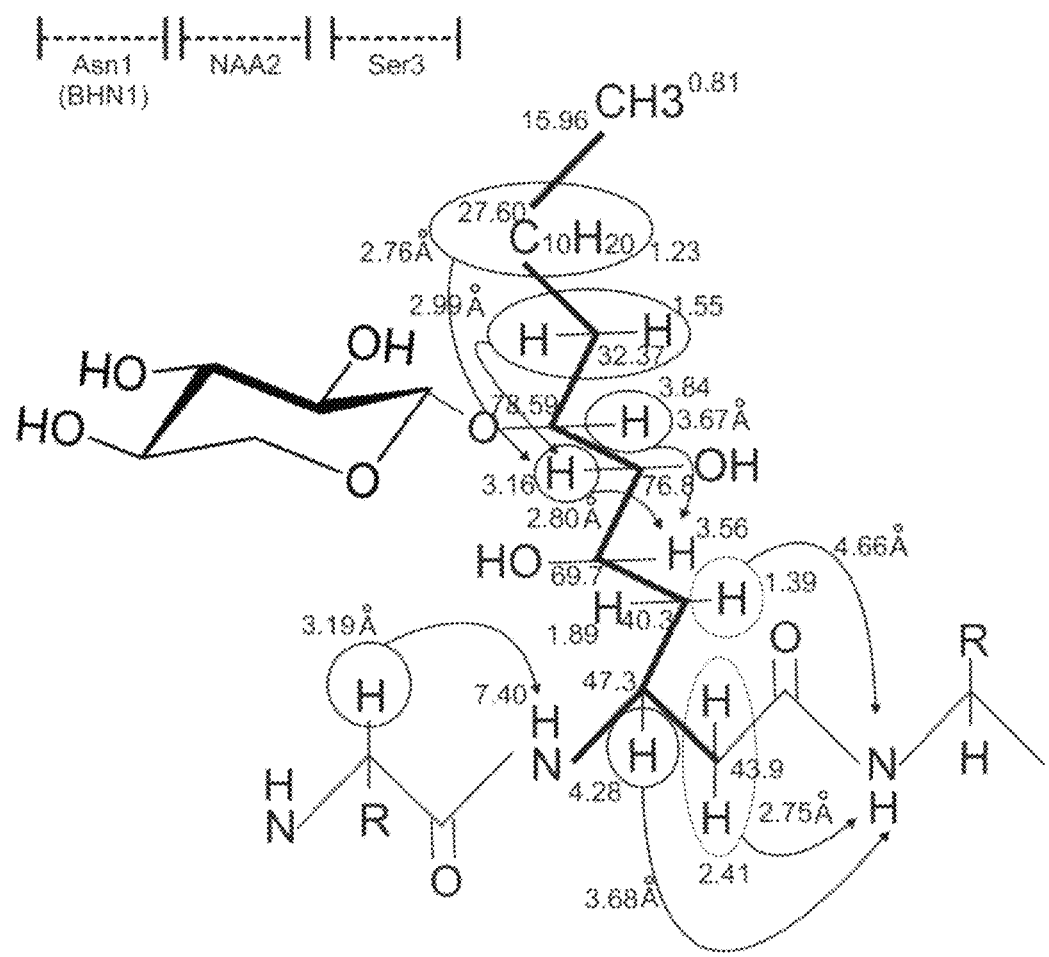
FIG. 1B is an illustration of the representative structure of novel amino acid NAA2. The chemical shift values (in ppm) are shown next to their respective atoms. NOE values written next to the circles and arrows designate the proton interactions. The thick line width represents coupling between protons identified in the COSY spectrum.
Figure 2A:
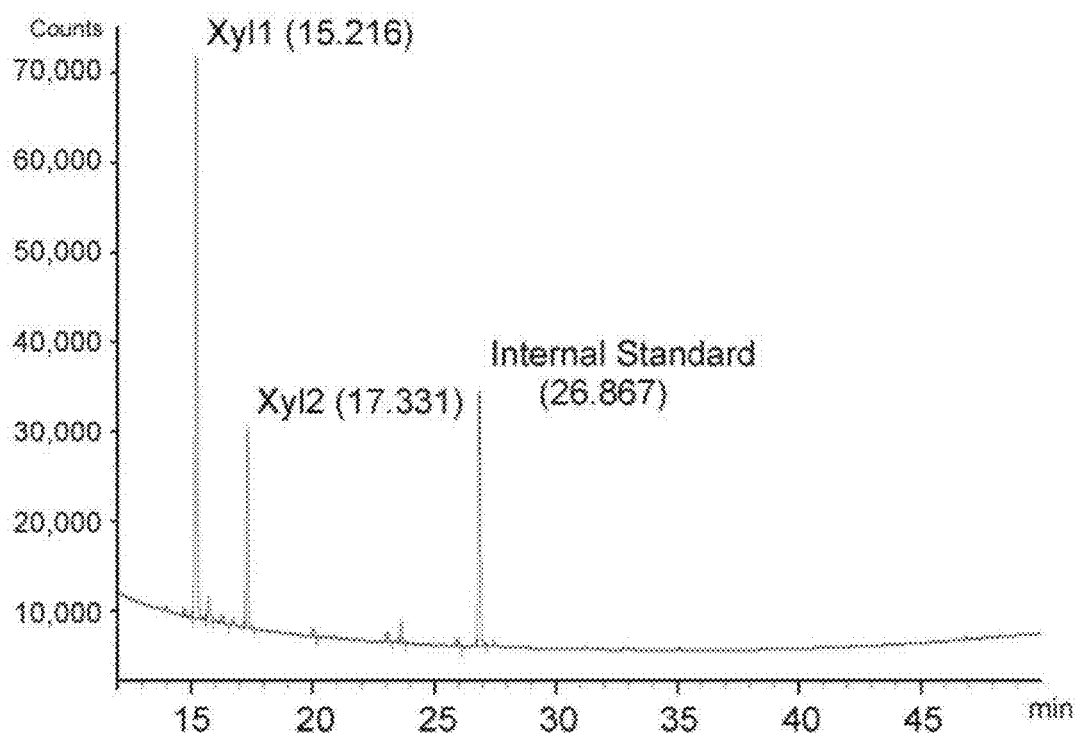
FIG. 2A is a graphical illustration of the GC chromatogram of a standard of xylose (A); internal standard was added to both samples. Xylose standard showed two peaks (Xy11 and Xy12).
Figure 2B:
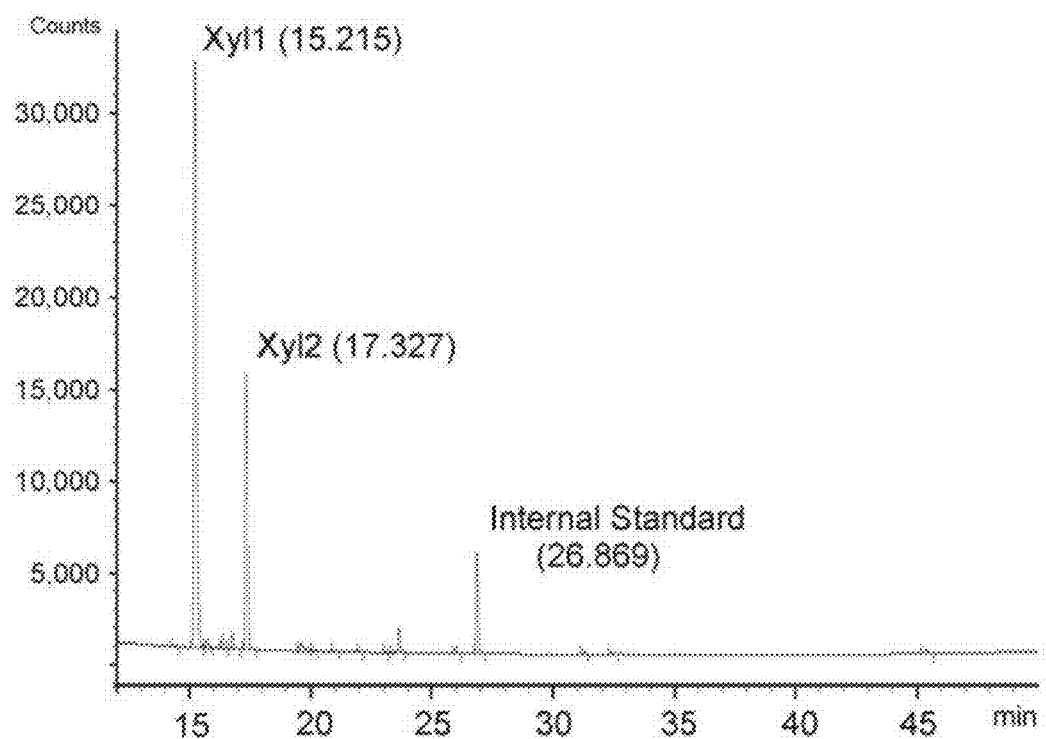
FIG. 2B is a graphical illustration of the GC chromatogram of the glycan from occidiofungin (B): internal standard was added to both samples. Occidiofungin glycan was identified as xylose based on the identical migration times of both peaks.
Figure 3B:
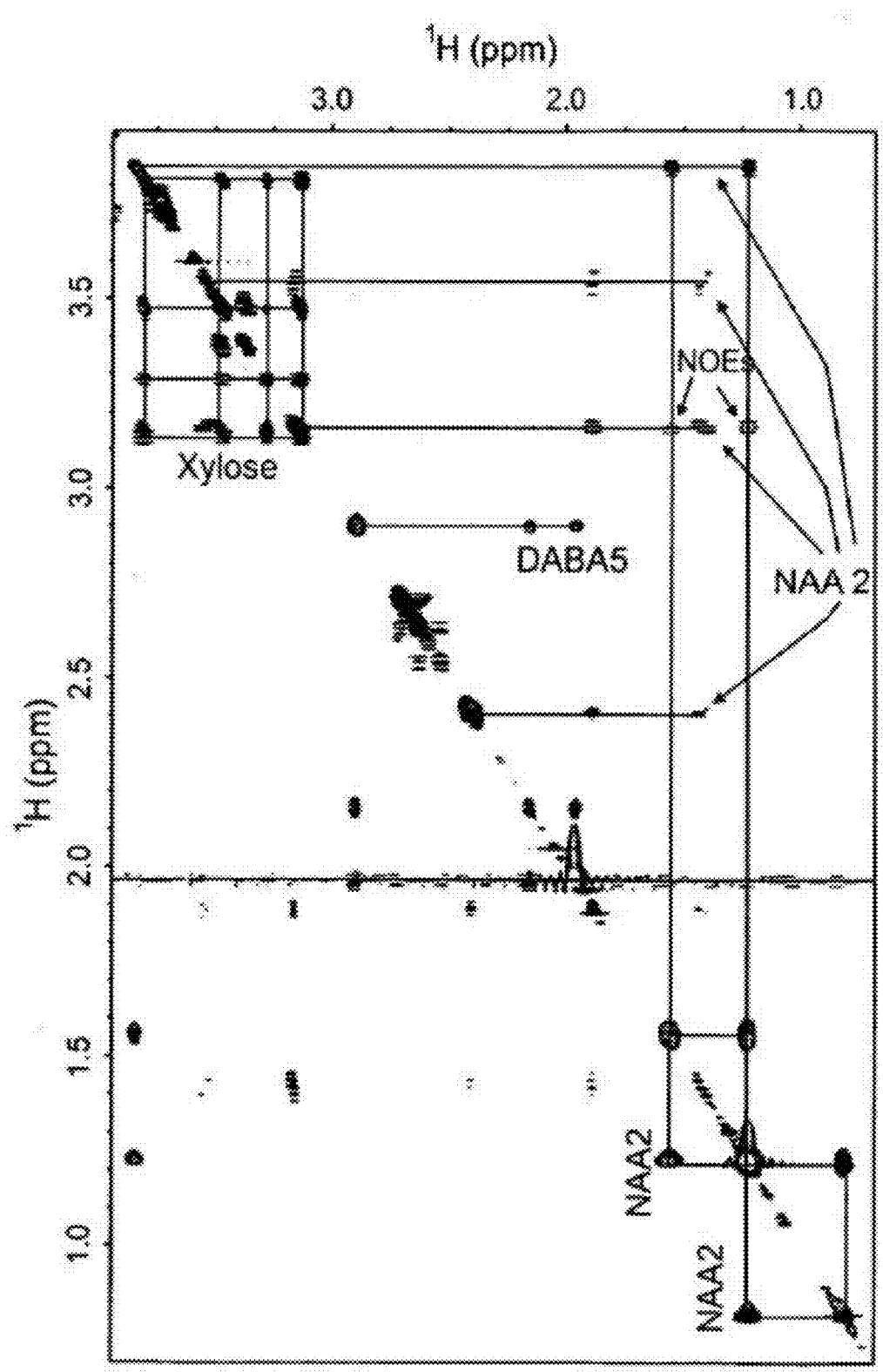
FIG. 3B is a graphical illustration of the NOESY NMR spectra of occidiofungin. Expansion of the NOESY 2D NMR spectra shows the chemical shifts of the short acyl group and xylose sugar in occidiofungin. NOEs (colored in grey) between the protons of terminal carbons of NAA2 (1.55 and 1.23 ppm) and C6 (3.16 ppm) of the NAA2 are differentiated by arrows.

Occidiofungin A is composed of an Asn 1-novel amino acid 2 (NAA2)-Ser3-β-hydroxy Tyr4-DABA5-Gly6-Asn7-Ser8 (FIG. 1A). Numerical assignment of the amino acids is attributed to sequencing data outlining the location of the thioesterase domain in the NRPS complex: the location of the thioesterase domain typically designates the C-terminus of the oligopeptide. Residues 1 and 7 of occidiofungin A have a chemical shift pattern characteristic of an Asn residue (Table 1). NAA2 has a chemical shift pattern characteristic of a fatty amino acid with a xylose sugar attached (FIGS. 1B and 3B). Given the unique characteristics of this residue, its structure is discussed separately below. Residue 3 has a chemical shift pattern characteristic of a Ser residue. Residue 4 is a modified Tyr residue. The beta carbon is hydroxylated resulting in a remarkable downfield shift of the beta proton to 5.16 ppm. NOEs are observed between the delta protons of the aromatic ring to the beta proton of β-hydroxy Tyr, enabling definitive assignment of the aromatic proton frequencies. Residues 5, 6, and 8 have typical chemical shift patterns for DABA, Gly, and Ser, respectively. Occidiofungin B differs from occidiofungin A in that the β-carbon of Asn1 is hydroxylated, resulting in a β-hydroxy Asn residue at position 1. Hydroxylation of the beta carbon resulted in the beta proton shifting downfield to 4.24 ppm from 2.67 ppm. Furthermore, hydroxylation of beta carbon of Asn1 resulted in noticeable changes in the chemical shills in the amide proton frequency of the NAA2, Ser3, Asn7, and Ser8, suggesting differences in the overall conformation of occidiofungin A and occidiofungin B. Definitive assignment of all the Asn residues and the β-hydroxy Asn residue in the antifungal compound came from the ROESY dataset in which ROEs from the beta protons to the delta protons of the amino group were observed (data not shown).

Figure 4A:
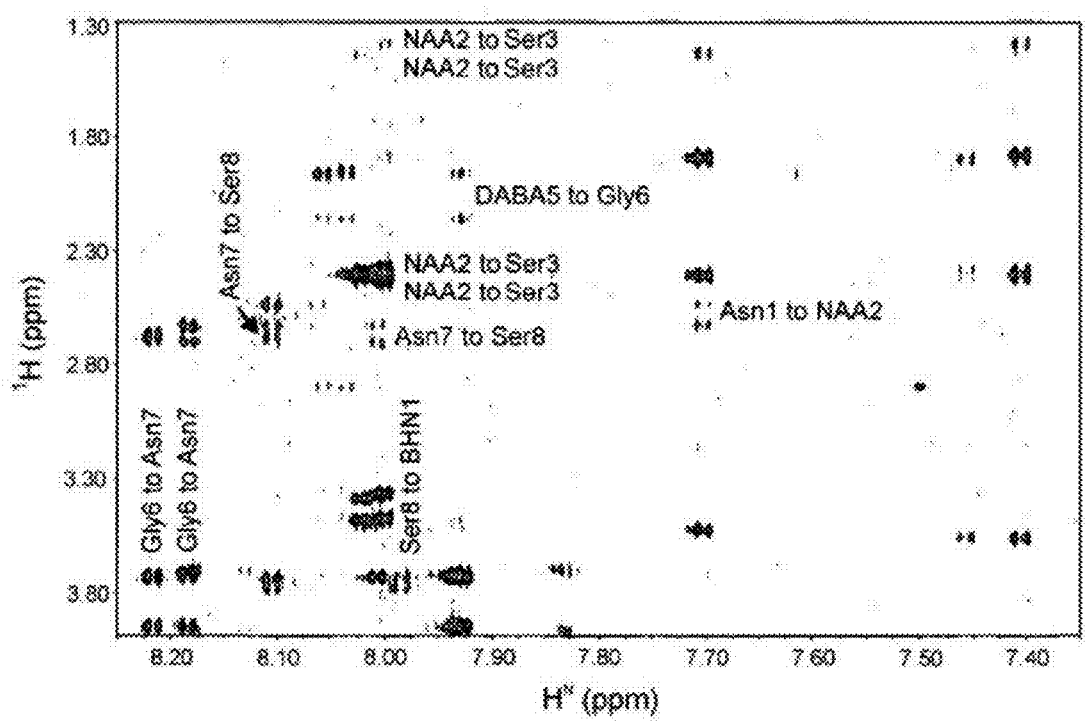
FIG. 4A is a graphical illustration of the NOESY NMR spectra of occidiofungin. The expansion shows the amide to alpha, and amide to side chain interactions. The respective amino acid interactions are labeled next to their inter-residue NOE's shown in red. Residues for occidiofungin A and occidiofungin B are presented in black and grey, respectively.
Figure 4B:
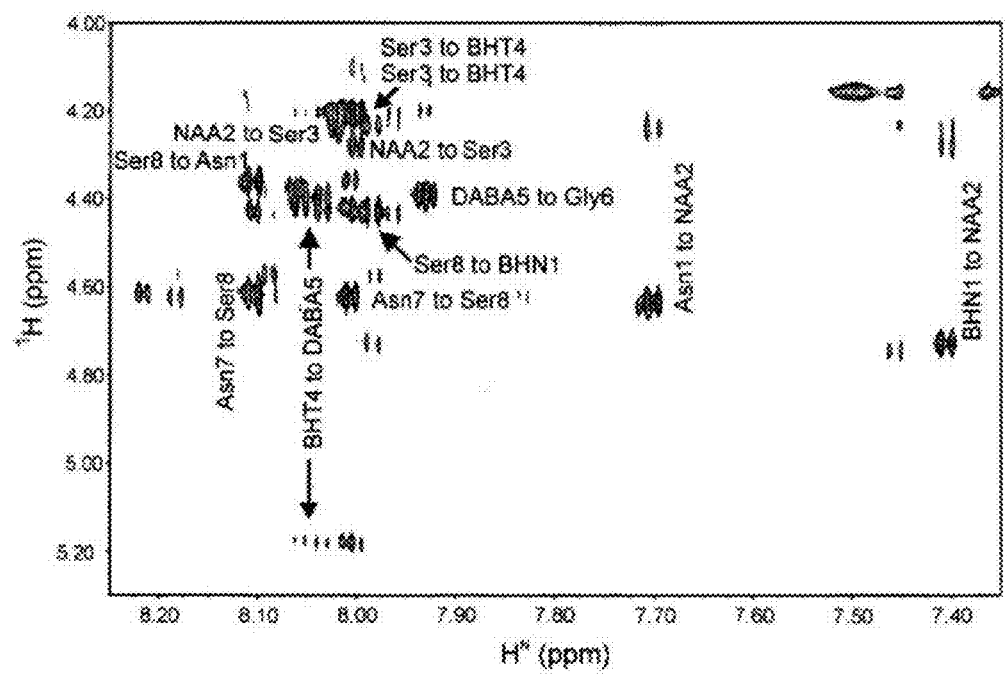
FIG. 4B is a graphical illustration of the NOESY NMR spectra of occidiofungin. The expansion shows the amide to alpha, and amide to side chain interactions. The respective amino acid interactions are labeled next to their inter-residue NOE's shown in red. Residues for occidiofungin A and occidiofungin B are presented in black and grey, respectively.

Residues 1 through 8 of occidiofungin A and occidiofungin B were sequentially assigned through an $H^{\alpha}_{i}$ and $H^{\beta}_{i}$ to $H^{N}_{i-1}$ sequential walk. NOE connectivities are shown in red in FIGS. 4A and 4B for occidiofungin A and occidiofungin B. A complete sequential walk could be done for both variants of occidiofungin. NOEs exist between $H^{\alpha}$ and $H^{\beta}$ of Asn1 and the $H^{\alpha}$ of β-hydroxy Asn1 to $H^{N}$ of the NAA2 of each variant. NOEs exist between protons on carbons 2, 3, and 4 (2.41, 4.28, and 1.39 ppm) of NAA2 to $H^{N}$ of Ser3 of each variant. Ser3 has an $H^\alpha$ proton NOE to $H^N$ of β-hydroxy Tyr4. NOEs exist between $H^\alpha$ and $H^\beta$ of β-hydroxy Tyr4 and 2,4-diaminobuttyric acid 5 (DABA5) to $H^N$ of DABA5 and Gly6, respectively. Gly6 has an $H^\alpha$ proton NOE to $H^N$ of Asn7 of each variant. Additional NOEs exist between $H^\alpha$ and $H^\beta$ of Asn7 and $H^N$ of Ser8 of each variant. Furthermore, evidence of the cyclic nature of the oligopeptide comes from NOEs between $H^\alpha$ of Ser8 of occidiofungin A and $H^\alpha$ and $H^\beta$ of Ser8 of occidiofungin B to $H^N$ of Asn1 and $H^N$ of β-hydroxy Asn1, respectively. $H^N_i$ to $H^N_{i-1}$ NOEs were observed between NAA2 to Ser3, DABA5 to Gly6, Gly6 to Asn7, and Asn7 to Ser8 for both occidiofungin A and occidiofungin B (data not shown). Additional $H^N_i$ to $H^N_{i-1}$ NOEs were observed between Asn1 to NAA2 and β-hydroxy Asn1 to NAA2 for occidiofungin A and occidiofungin B, respectively.

Due to the unique structure, a schematic of residue 2 is provided in FIG. 1B. The structural base of NAA2 is a Carbon 18 fatty acid. Presumably, this residue is formed by the ketoacyl synthase and transaminase found in the genomic region responsible for the synthesis of the anti fungal compound (Gu, Smith, and Lu, unpublished). Using the elemental assignments of a carbonyl as reference for the first carbon, the chemical shill assignments for carbon 1 through 18 is supported by NOE data. NOEs between protons on carbons 2, 3, and 4 (2.41, 4.28, and 1.39 ppm) of NAA2 to $H^N$ of Ser3 are observed. The intensities of the NOEs decrease as the distances of the protons to the $H^N$ of Ser3 increase (FIG. 1B). Furthermore, the terminal amino group on the novel amino acid residue is covalently linked to the preceding Asn residue's carbonyl group, as observed by the NOEs described above. Analyses of the chemical shifts in this region suggest that the NAA2 provides the base for attaching the xylose sugar (Table 1). The data support the presence of hydroxyl groups on carbons 5 and 6 (69.7 and 76.8 ppm) and attachment of the xylose sugar to carbon 7 (78.59 ppm) of the novel amino acid residue. The predicted chemical shift value for protons on a saturated carbon in this region would be approximately 1.7 ppm. The protons on carbons 5, 6 and 7 are significantly shifted downstream of this predicted value to 3.56 ppm, 3.16 ppm, and 3.84, respectively. The change in the chemical shifts of these protons suggests the presence of an electron withdrawing group, such as oxygen in their vicinity. It is predicted that the double bonded oxygen on carbons 5, 6, and 7, which would be present as part of fatty acid synthesis by the ketoacyl synthase, are reduced to a hydroxyl group, and subsequently the xylose sugar is attached to carbon 7 (78.59 ppm) via condensation reaction. NOEs between the terminal fatty acid protons (1.55 and1.23 ppm) exist to the proton on carbon 6 (3.16 ppm) of the novel amino acid residue (FIG. 1B), supporting the assignments. The Ser8 residue in the molecule could also support the attachment of the xylose. However, the lack of any notable changes in its predicted chemical shift values adds significance to the dramatic downstream shill of the $H^\beta$ proton observed in NAA2. The attachment of the xylose to other residues in the molecule would result in a loss of oxygen on the xylose molecule, resulting in a lower mass than what was observed in the mass spectrometry data described above. Consequently, carbon 7 (78.59 ppm) of NAA2 is the most plausible attachment site for the xylose. The HSQC data provided additional correlation between the protons of the NAA2 to the carbon resonances of the modified residue. For instance, the carbon resonance for carbon 4 had two distinguishable protons with resonances of 1.89 and 1.39 ppm (FIGS. 1A and 1B).

Figure 5B:
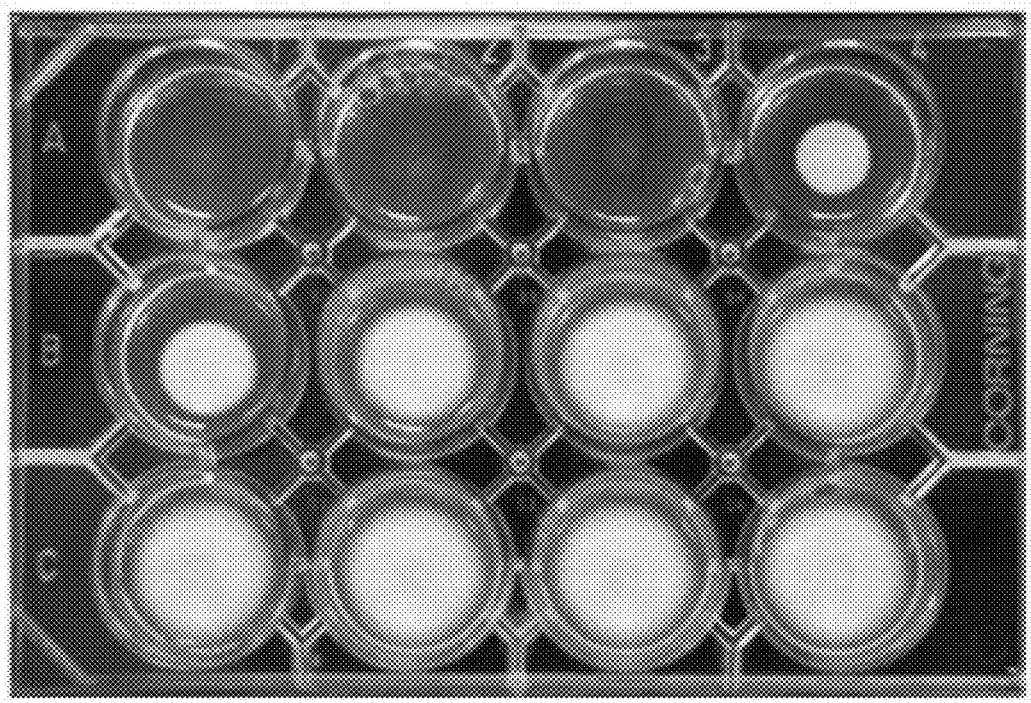
FIG. 5B is a pictorial illustration of spectrum of activity for occidiofungin. A representative bioassay plate is shown of *Geotrichum candidum*. Initial concentration in well A1 is 32 μg/mL and well C2 is the final concentration of 62.5 ng/mL. The last two wells serve as a negative control (no antifungal compound). Well A4 is a good representation of a MIC50, in which the growth of the fungus was inhibited by more than 50%.

Occidiofungin has a broad spectrum of antifungal activity. Occidiofungin demonstrated significant antifungal activity against a broad array of fungal plant and animal pathogens (FIGS. 5A and 5B). *R. solani* was the most sensitive of the fungi tested with an MIC of 2 mg/mL and exhibited significant growth inhibition at a concentration of 0.5 μg/mL. *A. fumigatus* and *A. niger*, which are common causes of invasive pulmonary aspereillosis, both were highly susceptible to occidiofungin with a MIC of 8 μg/mL and 4 μg/mL, respectively. Two related fungi, *Microsporum gypseum* and *Trichophyton mentagrophytes* which are both associated with dermatophytosis, were sensitive to occidiofungin with MICs of 4 μg/mL. Additional pathogenic fungi, *Penicillium* sp., *Alternaria alternata* and *Macrophomina phaseolina*, were shown to be sensitive to occidiofungin with an MIC of 32 μg/mL, 8 μg/mL and 2 μg/mL, respectively. The fungus *F. oxysporum* was the least sensitive to occidiofungin with a MIC >32 μg/mL. However, significant growth inhibition was observed at 16 μg/mL. *G. candidum*, a yeast pathogen of plants and animals, was significantly inhibited having an MIC of 8 μg/mL and remarkable growth inhibition at 4 μg/mL (FIG. 5B). *P. spinosum* and *P. ultimum* were the most sensitive to occidiofungin, with a MIC of 1 μg/mL and 2 μg/mL, respectively. These data indicate that occidiofungin has possible application as a potent broad spectrum antifungal agent against plant and animal fungal pathogens.

Figure 6:
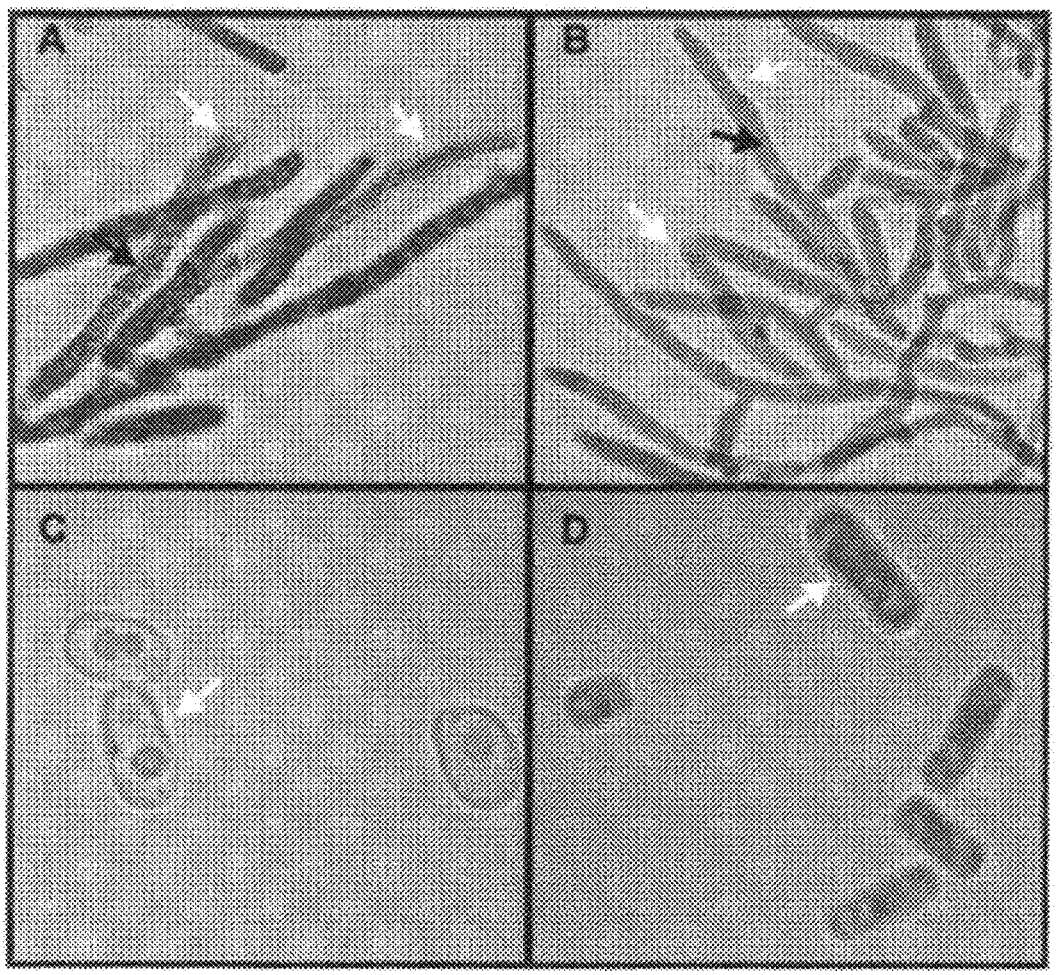
FIG. 6 is a pictorial representation of light microscopy. In panel A and B, significant hyphal morphological changes in *Rhizoctonia solani* grown in sub-inhibitory concentrations (panel A) are notably observed when compared to control (panel B). Black arrows point to the formation of intracellular inclusions and the white arrows point to membrane deformities. In panels C and D, Geotrichum candidum exposed to 4 μg/mL of occidiofungin for 48 hours (panel C) resulted in significant swelling of the cells, as compared to control (panel D).
Figure 7A:
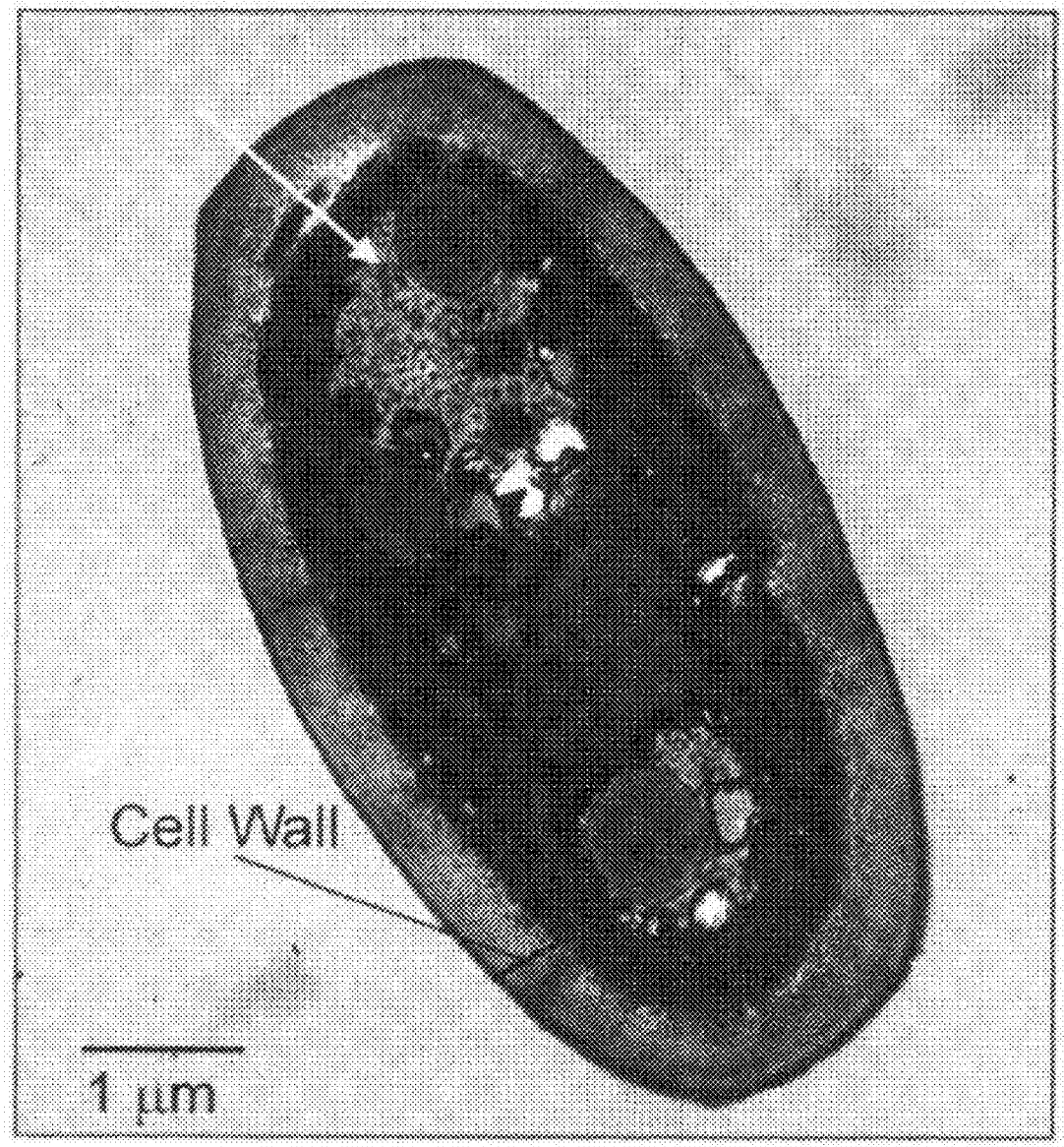
FIG. 7A is a pictorial representation of transmission electron microscopy and shows the untreated control test cell. Images were taken at a magnification of 8,000.
Figure 7B:
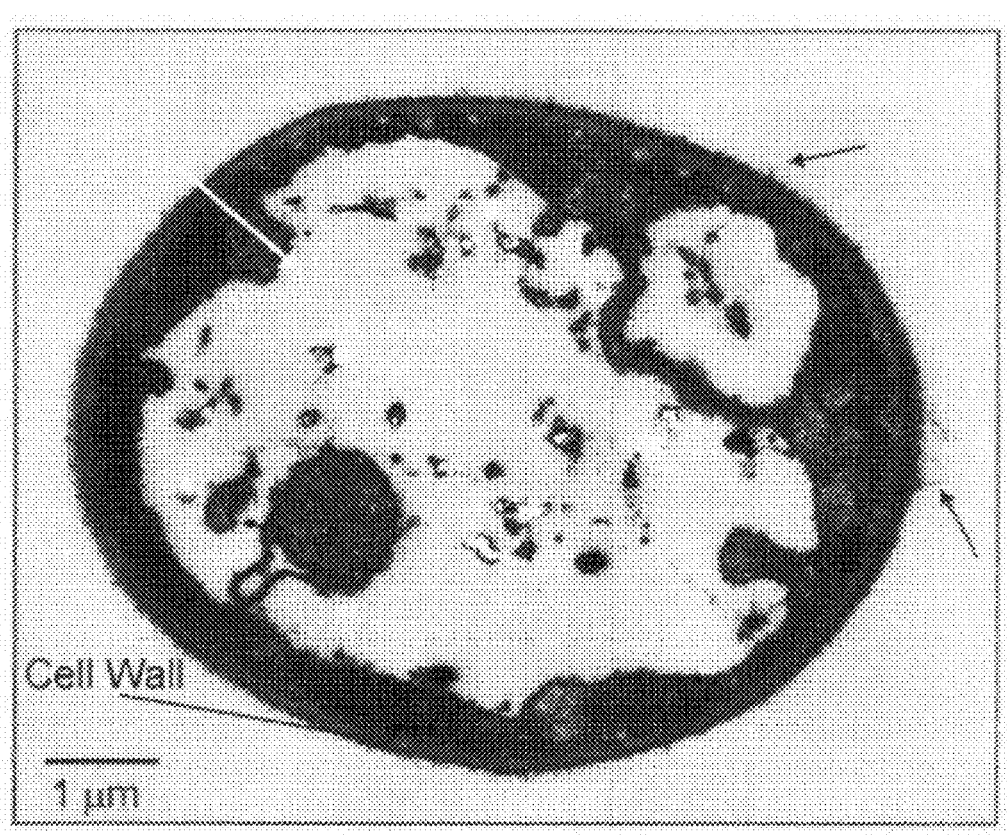
FIG. 7B is a pictorial representation of transmission electron microscopy showing *Geotrichum candidum* exposed to 4 μg/mL of occidiofungin for 48 hours, which sample resulted in remarkable morphological changes as compared to the untreated control test cell. Cell wall thickness is drastically reduced compare to the control. The exterior cell wall of treated *Geotrichum candidum* appears to be sloughing off (black arrow). The lack of contrast inside the treated sample (white arrow) suggests that the cell has lysed and effluxed cellular components. Images were taken at a magnification of 8,000.
Figure 7C:
FIG. 7C is a pictorial representation of transmission electron microscopy which shows a wider view containing several arthrospores exposed to occidiolungin. Images were taken at a magnification of 8,000.

Occidiofungin alters membrane integrity. Hyphae and cells of equivalent age were used in these studies. Hyphae of *R. solani* growing in subinhibitory concentrations of occidiofungin (0.5 μg/mL) were compared to hyphae of *R. solani* growing in the absence of the antifungal compound. There was more than a 50% reduction in growth of *R. solani* at this concentration (FIG. 5A). Occidiofungin induced significant hyphal morphological changes, with one of the most notable changes being the formation of intracellular inclusions (FIG. 6, panels A and B, black arrows). Another noticeable difference was the deformation of the tips of the hyphae and the undulated pattern of the cell membrane following exposure to occidiofungin (FIG. 6, panels A and B, white arrows). The same observation was made on hyphae morphology of *M. phaseolina* grown under subinhibitory concentrations (not shown). Arthrospores of *G. candidum* exposed to 4 μg/mL of occidiofungin for 48 hours showed amorphous shapes due to cellular swelling following exposure (FIG. 6, panels C and D) when compared with untreated cells. TEM data shows a dramatic decrease in cell wall thickness of *G. candidum* following exposure to subinhibitory concentrations of occidiofungin for 48 hours (FIGS. 7A, 7B, and 7C). In addition, what appears to be sloughing of the cell wall is present in the treated sample (FIGS. 7A and 7B, black arrows), which suggests that cell wall integrity is affected by exposure to occidiofungin. The lack of internal cellular contrast in the treated *G. candidum* also suggests that the cell has lysed (FIGS. 7A and 7B, white arrows). Presumably, the thinner cell wall is unable to maintain the osmotic pressure. No statement about swelling can be made from the TEM data, given that the arthrospores arc cylindrical and the chance of cross sectioning them is high. A wider view showing several arthrospores does show that sonic of the arthrospores do retain a cylindrical appearance (FIG. 7C); nonetheless, they all share the same morphological deformities internally and in the cell wall as seen in the arthrospore shown in FIG. 7B. These observations indicate that occidiofungin targets membrane integrity by disrupting cell wall formation and that occidiofungin may inhibit enzyme function, since the formation of visible inclusion bodies are generally attributed to substrate accumulation.

Discussion

The findings from this study include: the elucidation of the complete covalent structure of occidiofungin which contains a novel amino acid: characterization of the broad spectrum antifungal activity of occidiofungin; and in vivo observation of cellular inclusions and membrane instability following exposure to the antifungal compound.

Structural characterization confirms that occidiofungin is a unique antifungal agent. All of the mass spectrometry and NMR data presented above are in complete agreement and support the structure of occidiofungin shown in FIGS. 1A and 1B. The structural data provided unambiguous amino acid assignments enabling us to distinguish between the two structural variants of occidiofungin, occidiofungin A and occidiofungin B. A complete sequential walk across the backbone of each molecule was shown. Furthermore, NOEs from the C-terminal residue Ser8 to Asn1 of occidiofungin A and β-hydroxy Asn 1 of occidiofungin B confirm the cyclic nature of the oligopeptide that was predicted previously.

A novel amino acid was identified and is well-characterized by the NMR data. The importance of this unique residue for the anti fungal activity is unknown, but is an area of enormous interest by our group. In addition, two amino acid derivatives, β-hydroxy Asn (exclusive to occidiofungin B) and β-hydroxy Tyr were identified in the NMR data (Table 1). Chromatographic separation of each variant has not yet been accomplished. Therefore, it is not yet known if the hydroxylation of the beta carbon of Asn 1 is important for the bioactivity of the compound. The dramatic shift in the amide frequencies of the residues near β-hydroxy Asn 1 docs suggest that the conformation of the peptide did change following hydroxylation of the beta carbon of Asn 1.

The exact mechanism of activity of occidiofungin is not known, but this study provides a solid base to begin experiments to elucidate the mechanism of action. Occidiofungin demonstrated strong inhibitory activity against two *Pythium* species. *Pythium* is not a true fungus and ergosterol is not present as a main sterol in their cellular membranes; consequently, it is insensitive to antifungals that target ergosterol. Thus, the antifungal activity of occidiofungin presumably does not involve binding ergosterol or inhibiting ergosterol synthesis. It is also important to note that the cell wall of *Pythium* does not contain chitin, and that this oomycete contains a great amount of β-glucan in its cell wall. Thus, it is also not likely that occidiofungin targets chitin synthesis.

The morphology of fungi exposed to occidiofungin resembles the morphology reported in the literature of fungi exposed to cchinocandins, suggesting that occidiofungin may target glucan synthesis. *A. fumigants* exposed to inhibitory concentrations of micafungin, an cchinocandin, displayed hyphal burst and showed undulated membranes and deformed hyphae tips at sub-inhibitory concentrations. *Candida albicans* exposed to lethal dosage of cchinocandins induce swelling and at sub-inhibitory dosage abnormal morphological changes were observed on the membrane. The formation of aberrant membrane morphology in *A. fumigatus* is similar to what was observed when *R. solani* and *M. phaseolina* were grown under sub-inhibitory concentrations and the cellular swelling of *C. albicans* resembles what was observed for *Geotrichum candidum* exposed to a subinhibitory dose of occidiofungin. Interestingly, *Fusarium* spp. are resistant to cchinocandins. The mechanism of resistance is attributed to natural mutants in the catalytic subunit of the (1,3)-β-glucan synthase enzyme and natural differences in cell wall structure, specifically, *Fusarium* spp. possess less 1,3-β-glucans. While the MIC of *F. oxysporum* was >32 µg/mL in this study, occidiofungin did dramatically slow the growth of this fungus at 16 µg/mL. Further studies will explore whether occidiofungin inhibits glucan fungal cell wall synthesis, in particular its ability to inhibit (1,3)-β-glucan synthase. Cell wall formation and responses to cell wall damage involves an intricate cell signaling network, which orchestrates communication between the fungal cell wall surface to biosynthetic enzymes for synthesis and repair. Consequently, the exact mechanism of action of occidiofungin could involve a completely novel target.

A composition comprising the present invention can be administered to a subject animal or plant in a therapeutically effective amount, depending on the severity of the infection or disease, thereby preventing or lessening any short- or long-term effects of fungal infection.

This disclosure has for the first time described and fully characterized a set of novel and extremely effective antifungal compounds for applications to prevent and reduce a broad range of fungal infections in human, animal, and plant subjects, as well as the novel isolated bacterial strain that produces the anti fungal compounds.

The above detailed description is presented to enable any person skilled in the art to make and use the invention. Specific details have been disclosed to provide a comprehensive understanding of the present invention and are used for explanation of the information provided. These specific details, however, are not required to practice the invention, as is apparent to one of ordinary skill in the art. Descriptions of specific applications, analyses, and calculations are meant to serve only as representative examples. Various suitable changes, modifications, combinations, and equivalents to the preferred embodiments and additional or different interactions and materials and resultant advantages will be readily apparent to one skilled in the art and the general principles defined herein may be applicable to other embodiments and applications while still remaining within the spirit and scope of the invention. The claims and specification should not be construed to unduly narrow the complete scope of protection to which the present invention is entitled. It should also be understood that the figures are presented for example purposes only. No intention exists for the present invention to be limited to the embodiments shown and the invention is to be accorded the widest possible scope consistent with the principles and features disclosed herein.

TABLE 1

| | | Chemical Shifts | | |
|---|---|---|---|---|
| Amino Acid | $H^N$ | $H^\alpha$ | $H^\beta$ | Other Proton |
| Asn1 | 8.21 | 4.62 (53.20) | 2.67 (39.98) | 7.43* |
| [BHN 1] | 7.98 | 4.73 (58.74) | 4.24 | 7.49 |
| NAA2 | 7.67 | | | C2: 2.41 (43.90), C3: 4.23 (47.36), C4: 1.89 (40.32), 1.44 (40.32), C5: 3.52 (69, 70), C6: 3.17 (76.88), C7: 3.84 (78.59), C8: 1.55 (32.37), C9-17: 1.23 (27.60), C18: 0.81 (15.96) |

TABLE 1-continued

Chemical Shifts

| Amino Acid | $H^N$ | $H^\alpha$ | $H^\beta$ | Other Proton |
|---|---|---|---|---|
| [NAA2] | 7.40 | | | C2: 4.28 (47.36), C3: 2.41 (43.90), C4: 1.89 (40.32), 1.39 (40.32), C5: 3.56 (69, 70), C6: 3.16 (76.88), C7: 3.84 (78.59), C8: 1.55 (32.37), C9-17: 1.23 (27.60), C18: 0.81 (15.96) |
| Ser 3 | 8.02 | 4.20 (58.54) | 3.49, 3.35 (64.05) | |
| [Ser 3] | 8.00 | 4.20 (58.54) | 3.47, 3.35 (64.05) | |
| BHT 4 | 8.00 | 4.42 (63.18) | 5.16 (74.06) | 7.17, 6.76 |
| DABA5 | 8.04 | 4.39 (53.88) | 2.15, 1.96 (31.29) | 2.90 (39.75), 7.49 |
| Gly 6 | 7.93 | 3.94, 3.72 (45.06) | | |
| Asn 7 | 8.18 | 4.63 (53.13) | 2.70, 2.63 (38.38) | 7.40* |
| [Asn 7] | 8.21 | 4.62 (53.13) | 2.67 (38.58) | 7.43* |
| Ser 8 | 8.00 | 4.35 (58.27) | 3.73 (64.24) | |
| [Ser 8] | 8.10 | 4.43 (58.27) | 3.76 (64.24) | |
| Xylose | | | | 4.30, 3.81 (67.90), 3.48 (72.08), 3.28 78.47), 3.14 (67.97) |

Proton chemical shift values are from a TOCSY experiment. Chemical shifts in parentheses are $^{13}C$ values from the HSQC experiment. Distinc chemical shift values for occidiofungin B are shown in brackets.
*indicates chemical shift values from the ROESY experiment.

REFERENCES CITED

Cook, R. R., and Baker, K. F. (1983) The nature and practice of biological control of plant pathogens. *American Phytopathological Society*, St. Paul, Minn.

Lu, S-E., Woolfolk, S., and Caceres, J. (2005) Isolation and identification and genetic analysis of rhizobacteria antagonistic to plant soilborne fungal pathogens. *Phytopathology* 95, 62-63.

Gu, G. Y., Smith, L., Wang, N., Wang, H., and Lu, S -E. (2009) Biosynthesis of an antifungal oligopeptide in *Burkholderia contaminans* strain MS14. *Biochem. Biophys. Res. Commun.* 380, 328-332.

Gu, G., Wang, N., Chaney, N., Smith, L., and Lu, S-E. (2009) AmbR1 is a key transcriptional regulator for production of antifungal activity of *Burkholderia contaminans* strain MS14. *FEMS Microbial. Lett.* Accepted May 5, 2009.

Ghannoum, M. G., and Rice, L. B. (1999) Antifungal Agents: Mode of Action, Mechanisms of Resistance, and Correlation of these Mechanisms with Bacterial Resistance. *Clin. Microbiol. Rev.* 12, 501 -517.

Kavanagh, K. (2007) New Insights in Medical Mycology, Springer, New York, N.Y.

Lorian, V. (2005), Antibiotics in laboratory medicine, Lippincott Williams & Wilkins, Philadelphia, Pa.

Hashimoto, S. (2009) Micafungin: a sulfated echinocandin. *J. Antibiot.* 62, 27-35.

Ikeda, F., Tanaka, S., Ohki, H., Matsumoto, S., Maki, K., Katashima, M., Barrett, D., and Aoki, Y. (2007) Role of micafungin in the antifungal armamentarium, *Curr. Medic. Chem.* 14, 1263-1275.

de Groot, P. W. J., de Boer, A. D., Cunningham, J., Dekker, H. L., de Jong, L., Hellingwerf, K. J., de Koster, C., and Klis, F. M. (2004) Proteomic analysis of *Candida albicans* cell walls reveals covalently bound carbohydrate-active enzymes and adhesins. *Eukaryot. Cell* 3, 955-965, Klis, F. M., de Groot, P., and Hellingwerf, K. (2001) Molecular organisation of the cell wall of *Candida albicans*. *Med. Mycol.* 39, 1-8.

Munro, C. A. and Gow, N. A. R. (2001) Chitin synthesis in human pathogenic fungi. *Med. Mycol.* 39.41-53, Romero, C. (2002) The genetic complexity of chitin synthesis in fungi. *Curr. Genet.* 91, 367-378.

Douglas, C. M., D'Ippolito, J. A., Shei, G. J., Meinz, M., Onishi, J., Marrinan, J. A., Li, W., Abruzzo, G. K., Flattery, A., Bartizal, K., Mitchell, A., and Kurtz, M. B. (1997) Identification of the FKS1 gene of *Candida albicans* as the essential target of 1,3-beta-D-glucan synthase inhibitors. *Antimicrob. Agents Chemother.* 41, 2471-2479.

Chiarini, L., Bevivino, A., Dalmastri, C., Tabacchioni, S., and Visca, P. (2006) *Burkholderia cepacia* complex species: health hazards and biotechnological potential. *Trends Microbiol.* 14, 277-286.

Mahenthiralingam, E., Baldwin, A., and Dowson, C. G. (2008) *Burkholderia cepacia* complex bacteria: opportunistic pathogens with important natural biology. *J. Appl. Microbiol.* 104, 1539-1551.

Walker, L. A., Munro, C. A., de Bruijn, I., Lenardon, M. D., McKinnon, A., and Gow, N. A. R. (2008) Stimulation of chitin synthesis rescues *Candida albicans* from echinocandins. *PloS Patting.* 4(4), e1000040.

Nishiyama, Y., Hasumi, Y., Ueda, K., Uchida, K., and Yamaguchi, H. (2005) Effects of micafungin on the morphology of *Aspergillus fumigatus. J. Electron Microsc.* 54. 67-77.

Nakai, T., Hatano, K., Ikeda, F., and Shibuya, K. (2005) Electron microscopic findings for micafungin-treated experimental pulmonary aspergillosis in mice. *Med. Mycol.* 43, 439-445.

Angiolclla, L., Maras, B., Stringaro, A. R., Arancia, G., Mondello, F., Girolamo, A., Palamara, A, T., and Casson, A. (2005) Glucan-associated protein modulations and ultra-structural changes of the cell wall in *Candida albicans* treated with micafungin, a water-soluble, lipopeptidc antimycotic. *J. Chemother.* 17, 409-416.

Tomana, M., Prchal, J., Garner, L., Skalka, H., and Barker, S. (1984) Gas chromatographic analysis of lens monosaccharides. *J. Lab. Clin. Med.* 103, 137-142.

Renfrow, M. B., Cooper, H. J., Tomana, M Kulhavy, R., Hiki, Y., Toma, K., Emmett, M. R., Mestecky, J., Marshal, A. G., and Novak, J. (2005) Determination of aberrant 0-glycosylation in the IgAl hinge region by electron capture dissociation Fourier transform-ion cyclotron resonance mass spectrometry. *J. Biol. Chem.* 280,19136-19145.

Wüthrich, K. (1986) NMR of Proteins and Nucleic Acids. Wiley, New York.

Braunschweiler, L., and Ernst, R. R. (1983) Coherence Transfer By Isotropic Mixing—Application to Proton Correlation Spectroscopy. *J. Magn. Reson.* 53, 521-528.

Kumar, A., Ernst, R. R., and Wuthrich, K. (1980) A Two-Dimensional Nuclear Overhauser Enhancement (2D NOE) Experiment for the Elucidation of Complete Proton-Proton Cross-Relaxation Networks in Biological Macromolecules. *Biochem. Biophys. Res. Commun.* 95, 1-6.

Bothner-By, A. A., Stephens, R. L., Lee, J., Warren, C. D., and Jeanloz, R. W. (1984) Structure determination of a tetrasaccharide: transient nuclear Overhauser effects in the rotating frame. *J. Am. Chem. Soc.* 106, 811-813.

Bodenhausen, G., and Ruben, D. J. (1980) Natural abundance nitrogen-15 NMR by enhanced heteronuclear spectroscopy. *Chem. Phys. Lett.* 69, 185-188.

Hwang, T. L., and Shaka, A. J. (1995) Water suppression that works. Excitation sculpting using arbitrary waveforms and pulsed field gradients. *J. Magn. Reson. A*112, 275-279.

Dalvit, C. (1998) Efficient multiple-solvent suppression for the study of the interactions of organic solvents with biomolecules. *J. Biomol. NMR. SL*1, 437-444.

Shaka, A. J., Lee, C. J., and Pines, A. (1988) Iterative Schemes for Bilinear Operators—Application to Spin Decoupling. *J. Magn. Reson.* 77, 274-293.

Marion, D., Ikura, M., Tschudin, R., and Bax, A. (1989) Rapid Recording of 2D NMR-Spectra without Phase Cycling—Application to the Study of Hydrogen-Exchange in Proteins. *J. Magn. Reson.* 85, 393-399.

Kay, L. E., Keiffer, P., and Saarinen, T. (1992) Pure absorption gradient enhanced heteronuclear single quantum correlation spectroscopy with improved sensitivity. *J. Am. Chem. Soc.* 114, 10663-10665.

Boban, J. K., Plant, D., and Hurd, R. E. (1992) Improved Proton-Detected Heteronuclear Correlation Using Gradient-Enhanced z and zz filters. *J. Magn. Reson. A*101, 113.

Delaglio, F., Grzesiek, S., Vuister, G. W., Zhu, G., Pfeifer, J., and Bax, A. (1995) NMRpipe—a Multidimensional Spectral Processing System Based on Unix Pipes. *J. Biomol. NMR* 6, 277-293.

Johnson, B. A., and Blevins, R. A. (1994) NMRView—a Computer-Program for the Visualization and Analysis of NMR Data. *J. Biomol. NMR* 4, 603-614.

Gross, D., and DeVay, J. (1977) Production and purification of syringomycin, a phytotoxin produced by Pseudomonas syringae. *Physiol. Plant Pathol.* 11, 13-28.

Nishiyama, Y., Uchida, K., and Yamaguchi, H. (2002) Morphological changes of *Candida albicans* induced by micafungin (FK463), a water-soluble echinocandinlike lipopeptide. J. Electron Microsc. 51, 247-255.

Lin, S., Liehr, S., Cooperman, B. S., and Cotter, R. J. (2001) Sequencing cyclic peptide inhibitors of mammalian ribonucleotide reductase by electrospray ionization mass spectrometry. *J. Mass. Spectrom.* 36, 658-663.

Frias, H. V., Mendes, M. A., Cardozo, K. H. M., Carvalho, V. M., Tomazela, D., Colepicolo, P., and Pinto, E. (2006) Use of electrospray tandem mass spectrometry for identification of microcystins during a cyanobacterial bloom event. *Biochem. Biophys. Res. Commun.* 344, 741-746.

Felnagle, E. A., Jackson, E. E., Chan, Y. A., Podevels, A. M., Berti, A. D., McMahon, M. D., and Thomas, M. G. (2008) Nonribosomal peptide synthetases involved in the production of medically relevant natural products. *Mol. Pharm.* 5, 191-211.

Waelder, S., Lee, L., and Redfield, A. G. (1975) Nuclear magnetic resonance studies of exchangeable protons. I. Fourier transform saturation-recovery and transfer of saturation of the tryptophan indole nitrogen proton. *J. Am. Chem. Soc.* 97, 2927-2928.

Krishnan-Natcsan, S., and Chandrasekar, P. H. (2008) Current and future therapeutic options in the management of invasive aspergillosis. Drugs 68, 265-282.

Ngwogu, A. C., and Otokunefor, T. V. (2007) Epidemiology of dermatophytoses in a rural community in Eastern Nigeria and review of literature from Africa. *Mycopathologia* 164. 149-158.

Yaghmour, M. A., Inderbitzin, P., Bostock, R. M., and Michailides, T. J. (2008) Characterization of *Geotrichum candidum* causing sour rot of peaches and nectarines in California. *Phytopathology* 98, S175-S175.

Sfakianakis, A., Krasagakis, K., Steianidou, M., Maraki, S., Koutsopoulos, A., Kolicridis, D., Samonis, G., and Tosca, A. (2007) Invasive cutaneous infection with *Geotrichum candidum*—sequential treatment with amphotericin B and voriconazole. *Med. Mycol.* 45, 81-84.

Pereira, D. I. B., Santurio, J. M., Alves, S. H., Argenta, J. S., Potter, L., Spanamberg, A., and Ferreiro, L. (2007) Caspofungin in vitro and in vivo activity against Brazilian *Pythium insidiosum* strains isolated from animals. *J. Antimicrob. Chernother.* 60,1168-1171.

Argenta, J. S., Santurio, J. M., Alves, S. H., Pereira, D. I. B., Cavalheiro, A. S., Spanamberg, A., and Ferreiro, L. (2008) In vitro activities of voriconazole, itraconazole, and terbinafine alone or in combination against *Pythium insidiosum* isolates from Brazil. *Antimicrob. Agents Chernother.* 52. 767-769.

Popolo, L., Gualtieri, T., and Ragni, E. (2001) The yeast cell-wall salvage pathway. *Med. Mycol.* 39,111-121.

Levin, D. E. (2005) Cell wall integrity signaling in *Saccharomyces cerevisiae*. *Microbiol. Mol. Biol. Rev.* 69, 262-291.

Douglas, C. M. (2001) Fungal beta(1,3)-D-glucan synthesis. *Med. Mycol.* 39, 55-66.

We claim:

1. A method of treating a cell walled pathogen in a subject in need thereof, comprising:
   administering to the subject in need thereof an antifungal cyclic glycopeptide compound selected from the group consisting of occidiofungin A and occidiofungin B;
   wherein the antifungal cyclic glycopeptide compound is administered in a therapeutically effective amount sufficient to inhibit growth of the cell walled pathogen; wherein the cell walled pathogen is selected from the group consisting of an oomycotes pathogen and a fungal pathogen; and wherein the oomycotes pathogen is selected from the list consisting of *Pythium spinosum* and *Pythium ultimum* and the fungal pathogen selected from the list consisting of *Alternaria alternate, Aspergillus fumigatus, Aspergillus niger, Fusarium oxysporum, Geotrichum candidum, Candida albicans, Macrophomina phaseolina, Microsporum gypseum, Penicillium* sp., *Rhizoctonia solani*, and *Trichophyton mentagrophytes*.

2. The method of claim 1, wherein the subject in need thereof is a plant.

3. The method of claim 2, wherein the cell walled pathogen is the oomyrcotes pathogen and the therapeutically effective amount sufficient to inhibit growth of the oomycotes pathogen when isolated and grown in vitro is between about 62 nanograms per milliliter and about 32 micrograms per milliliter of said antifungal cyclic glycopeptide compound.

4. The method of claim 2, wherein the cell walled pathogen is the oomycotes pathogen and the therapeutically effective amount sufficient to inhibit growth of the oomycotes pathogen of the plant is between about 62 nanograms per milliliter and about 32 micrograms per milliliter of said antifungal cyclic glycopeptide compound.

5. The method of claim 1, wherein the subject in need thereof is a plant and the fungal pathogen is a plant fungal pathogen selected from the list consisting of *Alternaria alternate, Aspergillus niger, Fusarium oxysporum, Geotrichum candidum, Candida albicans, Macrophomina phaseolina, Rhizoctania solani,* and *Trichophyton mentagrophytes.*

6. The method of claim 5, wherein the therapeutically effective amount sufficient to inhibit growth of the plant fungal pathogen in vitro is between about 62 nanograms per milliliter and about 32 micrograms per milliliter of said antifungal cyclic glycopeptide compound.

7. The method of claim 5, wherein the therapeutically effective amount sufficient to inhibit growth of the plant fungal pathogen of the plant is between about 62 nanograms per milliliter and about 32 micrograms per milliliter of said antifungal cyclic glycopeptide compound.

8. The method of claim 1, wherein the subject in need thereof is an animal and the fungal pathogen is an animal fungal pathogen selected from the list consisting of *Alternaria alternate, Aspergillus fumigatus, Aspergillus niger, Geotrichum candidum, Candida albicans, Microsporum gypseum, Penicillium* sp., and *Trichophyton mentagrophytes.*

9. The method of claim 8, wherein the therapeutically effective amount sufficient to inhibit growth of the animal fungal pathogen when isolated and grown in vitro is between about 62 nanograms per milliliter and about 32 micrograms per milliliter of said antifungal cyclic glycopeptide compound.

10. The method of claim 8, wherein the therapeutically effective amount sufficient to inhibit growth of the animal fungal pathogen of the animal is between about 62 nanograms per milliliter and about 32 micrograms per milliliter of said antifungal cyclic glycopeptide compound.

11. The method of claim 1, wherein the oomycotes pathogen is selected from the list consisting of *Pythium spinosum* and *Pythium ultimum* and the fungal pathogen selected from the list consisting of *Alternaria alternate, Aspergillus fumigatus, Aspergillus niger, Geotrichum candidum, Candida albicans, Macrophomina phaseolina, Microsporum gypseum, Penicillium* sp., and *Trichophyton mentagrophytes.*

12. A method of disrupting membrane integrity in a cell walled pathogen by administering to a subject in need thereof an antifungal cyclic glycopeptide compound selected from the group consisting of occidiofungin A and occidiofungin B; wherein the cell walled pathogen is selected from the group consisting of an oomycotes pathogen and a fungal pathogen; and wherein the oomycotes pathogen is selected form the list consisting of *Pythium spinosum* and *Pythium ultimum* and the fungal pathogen selected from the list consisting of *Alternaria alternate, Aspergillus fumigatus, Asperigillus niger, Fusarium oxysporum, Geotrichum candidum, Candida albicans, Macrophomina phaseolina, Microsporum gypseum, Penicillium* sp., *Rhizoctonia solani,* and *Trichophyton mentagrophytes.*

13. The method of claim 12, wherein the subject in need thereof is a plant and the fungal pathogen is a plant fungal pathogen selected from the list consisting of *Alternaria alternate, Aspergillus niger, Fusarium oxysporum, Geotrichum candidum, Candida albicans, Macrophomina phaseolina, Rhizoctonia solani,* and *Trichophyton mentagrophytes.*

14. The method of claim 12, wherein the subject in need thereof is an animal and the fungal pathogen is an animal fungal pathogen selected from the list consisting of *Alternaria alternate, Aspergillus fumigatus, Aspergillus niger, Geotrichum candidum, Candida albicans, Microsporum gypseum, Penicillium* sp., and *Trichophyton mentagrophytes.*

15. The method of claim 13, wherein the oomycotes pathogen is selected from the list consisting of Pythium spinosum and Pythium ultimum and the fungal pathogen selected from the list consisting of *Alternaria alternate, Aspergillus fumigatus, Aspergillus niger, Geotrichum candidum, Candida albicans, Macrophomina phaseolina, Microsporum gypseum, Penicillium* sp., and *Trichophyton mentagrophytes.*

\* \* \* \* \*